United States Patent
Chang et al.

(10) Patent No.: US 11,030,741 B2
(45) Date of Patent: Jun. 8, 2021

(54) DENTAL THREE-DIMENSIONAL DATA PROCESSING DEVICE AND METHOD THEREOF

(71) Applicant: MEDIT CORP., Seoul (KR)

(72) Inventors: Minho Chang, Seoul (KR); Soobok Lee, Seoul (KR); Jiwoong Chang, Seoul (KR); Sungbin Im, Seoul (KR)

(73) Assignee: MEDIT CORP., Seoul (KR)

( * ) Notice: Subject to any disclaimer, the term of this patent is extended or adjusted under 35 U.S.C. 154(b) by 173 days.

(21) Appl. No.: 16/098,931

(22) PCT Filed: May 4, 2017

(86) PCT No.: PCT/KR2017/004714
§ 371 (c)(1),
(2) Date: Nov. 5, 2018

(87) PCT Pub. No.: WO2017/192020
PCT Pub. Date: Nov. 9, 2017

(65) Prior Publication Data
US 2019/0147591 A1 May 16, 2019

(30) Foreign Application Priority Data

May 4, 2016 (KR) .......................... 10-2016-0055609

(51) Int. Cl.
*G06T 7/00* (2017.01)
*A61B 6/00* (2006.01)
(Continued)

(52) U.S. Cl.
CPC .............. *G06T 7/0012* (2013.01); *A61B 6/00* (2013.01); *A61B 6/14* (2013.01); *A61C 9/0053* (2013.01);
(Continued)

(58) Field of Classification Search
CPC ................... G06T 7/0012; G06T 17/00; G06T 2207/10081; G06T 2207/10088;
(Continued)

(56) References Cited

U.S. PATENT DOCUMENTS

2007/0207441 A1* 9/2007 Lauren ............... A61C 13/0004
433/213
2009/0305185 A1* 12/2009 Lauren ................. A61C 9/0053
433/29
(Continued)

FOREIGN PATENT DOCUMENTS

JP 10-295707 A 11/1998
JP 2010-158275 A 7/2010
(Continued)

OTHER PUBLICATIONS

International Search Report for PCT/KR2017/004714 dated Jul. 11, 2017 from Korean Intellectual Property Office.

*Primary Examiner* — Michael R Neff
(74) *Attorney, Agent, or Firm* — Paratus Law Group, PLLC (57) ABSTRACT

A dental three-dimensional data processing device, including: an input unit for receiving teeth data, and image data of a human face; a control unit for generating three-dimensional alignment data by combining and aligning the teeth data and the image data; a movement extraction unit for generating trajectory data by analyzing the movement of teeth or temporomandibular joint from the image data; and a simulation unit for simulating the movement of the teeth or the temporomandibular joint by applying the trajectory data to the alignment data.

19 Claims, 7 Drawing Sheets

(51) Int. Cl.
*A61B 6/14* (2006.01)
*G06F 30/20* (2020.01)
*A61C 9/00* (2006.01)
*G06T 17/00* (2006.01)

(52) U.S. Cl.
CPC .............. *G06F 30/20* (2020.01); *G06T 17/00* (2013.01); *G06T 2207/10081* (2013.01); *G06T 2207/10088* (2013.01); *G06T 2207/30036* (2013.01)

(58) Field of Classification Search
CPC . G06T 2207/30036; G06F 30/20; A61B 6/00; A61B 6/14; A61C 9/0053
USPC ........................................................ 382/128
See application file for complete search history.

(56) References Cited

U.S. PATENT DOCUMENTS

| | | | |
|---|---|---|---|
| 2014/0294273 A1 | 10/2014 | Jaisson | |
| 2015/0132716 A1* | 5/2015 | Kusch | A61B 5/055 433/140 |
| 2015/0359614 A1 | 12/2015 | Sachdeva et al. | |

FOREIGN PATENT DOCUMENTS

| | | |
|---|---|---|
| KR | 10-0750279 B1 | 8/2007 |
| KR | 10-2013-0008236 A | 1/2013 |
| KR | 10-2013-0048202 A | 5/2013 |
| KR | 10-2015-0082428 A | 7/2015 |

\* cited by examiner

DENTAL THREE-DIMENSIONAL DATA PROCESSING DEVICE AND METHOD THEREOF

CROSS REFERENCE TO PRIOR APPLICATIONS

This application is a National Stage patent application of PCT International Patent Application No. PCT/KR2017/004714 (filed on May 4, 2017) under 35 U.S.C. § 371, which claims priority to Korean Patent Application No. 10-2016-0055609 (filed on May 4, 2016), which are all hereby incorporated by reference in their entirety.

BACKGROUND

The present disclosure relates to a dental three-dimensional data processing device and a method thereof, and more particularly, to a dental three-dimensional data processing device and a method thereof, which can diagnose the occlusion state thereof by determining a correlation between teeth and temporomandibular joint based on teeth data and image data of a face, and analyze the movements of the teeth and the temporomandibular joint.

Generally, human teeth are connected to temporomandibular joint to have a complicated movement according to the degree and direction of the movement of the temporomandibular joint.

Particularly, when the movement of the temporomandibular joint is deviated from the normal movement, it affects occlusion with a teeth model, such that it is necessary to determine the movement thereof.

Conventionally, in order to diagnose a patient who has a problem in the temporomandibular joint, a teeth model has been generated, then the teeth model has been mounted to an articulator to extract information on the occlusion from the articulator, and accordingly, the occlusion state has been determined.

However, the temporomandibular joint and the occlusion state of the teeth, for each human, are different and a masticatory habit is different, while the articulator has a certain shape and thereby cannot be corresponded to all humans, such that although the teeth model is corrected according to information on the occlusion state extracted from the articulator and is used to treat a patient, there has been a limitation to apply it to all patients.

In order to solve the problem, a method for tracking the movement thereof after mounting a predetermined device in the oral cavity of the patient was proposed, but the patient felt uncomfortable and the device was inserted into the oral cavity, such that since it was not possible to extract the accurate movement due to the interference with the movement of the teeth, there was a difficulty in diagnosis.

Accordingly, there is a need to provide a method for extracting the movements of the teeth and temporomandibular joint of the human more conveniently, and applying the movement of the temporomandibular joint to the teeth model to be used to correct the teeth model of the patient and treat the patient.

Meanwhile, Korean Patent Publication No. 10-2015-0082428 (published on Jul. 15, 2015) is disclosed as the related art that relates to a technology for estimating the movement trajectory from a specific scan to a next scan through three-dimensional scan in the oral cavity and compensating for the movement trajectory.

SUMMARY

The present disclosure relates to a dental three-dimensional data processing device and a method thereof, and an object of the present disclosure is to provide a dental three-dimensional data processing device and a method thereof, which diagnose the occlusion state by determining a correlation between teeth and temporomandibular joint based on teeth data and image data of a face, and diagnose a patient's condition by analyzing the movements of the teeth and the temporomandibular joint, thus generating and correcting a teeth model.

A dental three-dimensional data processing device in accordance with the present disclosure includes an input unit for receiving teeth data, and image data of a human face; a control unit for generating three-dimensional alignment data by combining and aligning the teeth data and the image data; a movement extraction unit for generating trajectory data by analyzing the movement of teeth or temporomandibular joint from the image data; and a simulation unit for simulating the movement of the teeth or the temporomandibular joint by applying the trajectory data to the alignment data.

In addition, the teeth data can include any one of scan data through a dental scanner, and facial bone data having the shape of the teeth measured through a Computed Tomography (CT) or a Magnetic Resonance Imaging (MRI).

In addition, the image data can be successive data acquired in real time.

In addition, the dental three-dimensional data processing device can further include a model generation unit for generating a teeth model reflecting the shape and movement of the teeth by designing the teeth based on the alignment data, the trajectory data, and the simulation result of the simulation unit.

In addition, the dental three-dimensional data processing device can further include a model correction unit for delivering it to the model generation unit by determining an interference factor of the teeth model generated by the model generation unit.

In addition, the model correction unit can input the correction data to the model generation unit by testing the teeth model according to the trajectory data to determine whether or not interference occurs.

In addition, the control unit can align the scan data and the image data, and determine the occlusion state accordingly.

In addition, the control unit can track the location and movement of the temporomandibular joint by aligning the facial bone data and the image data.

In addition, the image data can be image data scanning the face in which the teeth are exposed, and the control unit can align them by matching the teeth included in the image data with the teeth data.

In addition, the movement extraction unit can extract a feature point by analyzing the image data with respect to the moving teeth in real time, and can detect the movement of the teeth by tracking the movement of the feature point.

In addition, the movement extraction unit can detect the movement of the teeth by scanning a target attached to the teeth to analyze the movement of the target.

In addition, the dental three-dimensional data processing device can further include an output unit for outputting the result simulating so that the alignment data move according to the trajectory data in the simulation unit.

In addition, the simulation unit can display the movement trajectory of the teeth data and an interference surface on a screen, and the control unit can detect the rotation shaft of the temporomandibular joint through the simulation.

A dental three-dimensional data processing method in accordance with another aspect of the present disclosure includes receiving at least one of scan data through a dental scanner, and facial bone data having the shape of teeth measured through a CT or a MRI; receiving image data of a human face; generating alignment data by combining and aligning any one of the scan data and the facial bone data, and the image data; generating trajectory data by analyzing the movement of the teeth or temporomandibular joint from the image data; and simulating the movement of the teeth or the temporomandibular joint by applying the trajectory data to the alignment data.

In addition, the dental three-dimensional data processing method can further include generating a teeth model reflecting the shape and movement of the teeth by designing the teeth in response to the alignment data, the trajectory data, and the simulation result.

In addition, the image data can include at least one of primary image data scanning a face where a human closes a mouth and is kept silent, and secondary image data scanning a face where human teeth are exposed.

In addition, the receiving the image data can recognize a distance using data scanning the human face, generate facial three-dimensional data as the image data by performing color texture mapping, and extract a Frankfurt's plane, a Camper's plane, and an occlusion reference plane.

In addition, the generating the alignment data can align them by matching any one of the scan data and the facial bone data with the teeth included in the image data.

In addition, the generating the alignment data can align the scan data and the image data, and determine the occlusion state accordingly.

In addition, the generating the trajectory data can track the movement of the teeth or the temporomandibular joint from the image data input in real time.

In addition, the image data can be data scanning a target attached to the teeth, and the generating the trajectory data can detect the movement of the teeth by detecting the target from the image data.

In addition, the generating the trajectory data can extract a feature point of the teeth from the image data, and can generate the trajectory data by tracking the movement of the feature point.

In addition, the dental three-dimensional data processing method can further include correcting the teeth model by sensing teeth interference using the trajectory data with respect to the teeth model.

According to the dental three-dimensional data processing device and the method thereof in accordance with the present disclosure configured as described above, it is possible to extract the movements of the teeth and the temporomandibular joint to apply them to the teeth model, thus diagnosing the teeth state more accurately and precisely and analyzing the occlusion state according to the movements of the teeth and the temporomandibular joint; to accurately analyze the patient's condition based on the movement and the occlusion state, thus establishing treatment measures; and to generate and correct the teeth model suitable for the patient's condition, thus enhancing the treatment effect.

DETAILED DESCRIPTION

The advantages and features of the present disclosure and the method for achieving them will become apparent with reference to the embodiments described in detail below with reference to the accompanying drawings. The present disclosure can, however, be embodied in various forms and should not be construed as limited to the embodiments disclosed herein; these embodiments are only provided so that this disclosure will be thorough and complete and will fully convey the scope of the disclosure to those skilled in the art to which the present disclosure pertains; and the present disclosure is only defined by the scope of the claims. Like reference numerals refer to like elements throughout the specification.

Hereinafter, embodiments of the present disclosure will be described in detail with reference to the drawings.

Figure 1:
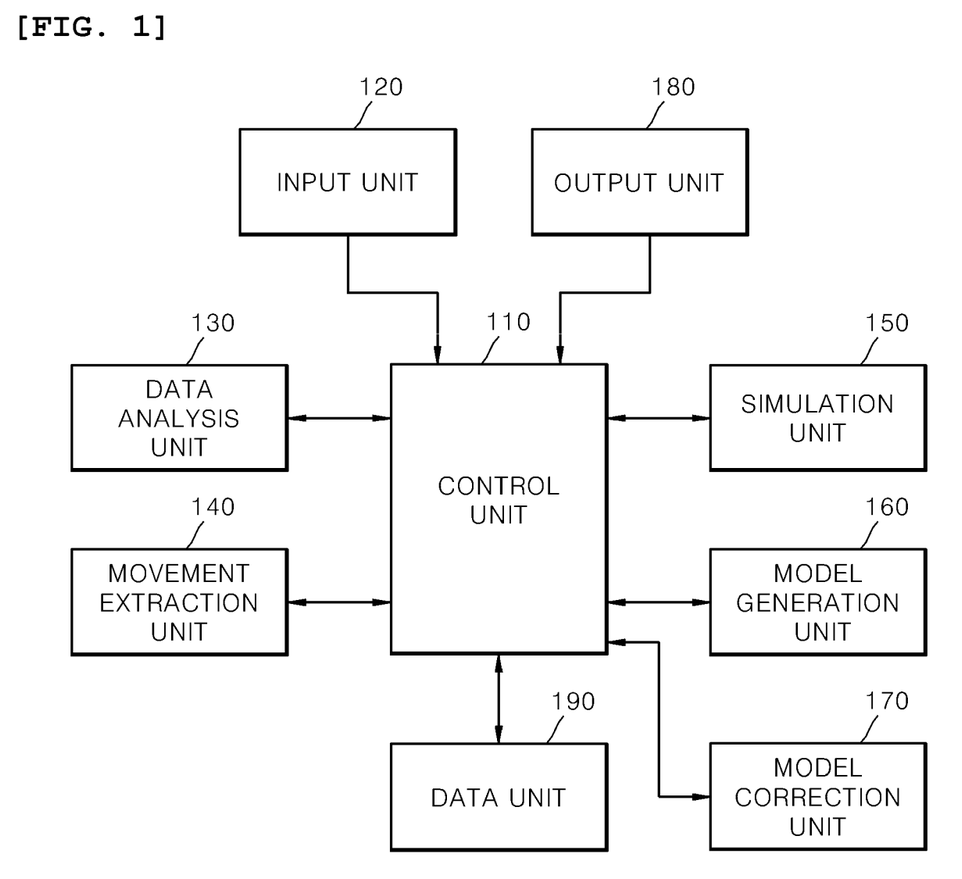
FIG. 1 is a block diagram schematically illustrating a configuration of a dental three-dimensional data processing device in accordance with the present disclosure.

FIG. 1 is a block diagram schematically illustrating a configuration of a dental three-dimensional data processing device in accordance with the present disclosure.

As illustrated in FIG. 1, the dental three-dimensional data processing device in accordance with the present disclosure includes an input unit 120, a data analysis unit 130, a movement extraction unit 140, a simulation unit 150, a model generation unit 160, a control unit 110, a model correction unit 170, an output unit 180, and a data unit 190.

The input unit 120 includes at least one input means for receiving data for generating a teeth model.

First, the input unit 120 receives teeth data and image data of a human face. Herein, the teeth data includes any one of scan data through a dental scanner and facial bone data having the shape of the teeth measured through a CT or a MRI.

In order to acquire the scan data through the dental scanner, the input unit 120 can use the dental scanner or a dental three-dimensional scanner, and can also include a photographing means for photographing the movement. The input unit 120 receives the two-dimensional or three-dimensional scan data acquired through the scanner or the photographing means.

In addition, in order to acquire the facial bone data having the shape of the human teeth, the input unit 120 can be connected to a device such as an X-ray, a Computed Tomography (CT), or a Magnetic Resonance Imaging (MRI) to receive the facial bone data having the shape of the teeth, and to receive the previously photographed and stored data.

In addition, the input unit 120 receives image data of the human face photographed with different expressions separately from the teeth data. Herein, the image data includes image data (primary image data) scanning a face where a human closes a mouth and is kept silent, and image data (secondary image data) scanning a face where the teeth are exposed. Herein, the image data are data input in real time, preferably successive data, and can be the two-dimensional or three-dimensional scan data.

Meanwhile, the output unit 180 outputs the teeth data or the image data input through the input unit 120 to a screen, and outputs the progressing state of the entire procedure of data processing. In addition, the output unit 180 outputs the movement of the teeth according to the movement extraction or the simulation to the screen. Herein, the output unit 180 can include a display means for outputting and displaying data, and can further include a speaker or an operation lamp for outputting a progressing state and a warning sound.

The data unit 190 stores the teeth data and the image data input through the input unit 120, data generated during operations of the data analysis unit 130 and the control unit 110, and data of a teeth model generated by the model generation unit 160 that will be described later.

The data analysis unit 130 analyzes the teeth data and the image data of the human face input through the input unit 120 so that the combination of the teeth data and the image data is easy. Specifically, the data analysis unit 130 can recognize a distance based on the image data scanning the human face, generate facial three-dimensional data as the image data by performing color texture mapping, and extract a Frankfurt's plane, a Camper's plane, an occlusion reference plane, etc.

Meanwhile, the movement extraction unit 140 extracts a feature point by analyzing the image data with respect to the moving teeth in real time, and detects the movement of the teeth by tracking the movement of the feature point. The movement extraction unit 140 generates the trajectory data of the teeth by tracking the movement of the feature point.

That is, the movement extraction unit 140 acquires a three-dimensional coordinate by analyzing the teeth data of the movement in real time through the image data of the face input in real time. The movement extraction unit 140 can generate the trajectory data by tracking the movement of the acquired coordinate, and extract the movements of the teeth and the temporomandibular joint that are different for each human.

The control unit 110 aligns them by receiving the input teeth data and image data, and data having the movement of the teeth, and determines the occlusion state accordingly.

Specifically, the control unit 110 can determine the occlusion state accordingly by aligning the scan data in the teeth data and the image data, thus utilizing them for diagnosis. In addition, the control unit 110 can track the location and movement of the temporomandibular joint by aligning the facial bone data in the teeth data and the image data. The image data are data measuring an actual human face, such that it is possible to accurately perform the determination of the occlusion state or the tracking of the location and movement of the temporomandibular joint, thus further increasing accuracy of diagnosis.

Meanwhile, the control unit 110 generates three-dimensional data occluded by aligning the input teeth data, that is, the scan data or the facial bone data photographed by a CT, and the facial image data. Herein, when aligning the facial bone data photographed by the CT and the image data, the control unit 110 aligns them based on the temporomandibular joint.

The control unit 110 receives secondary image data scanning a face where a human bites the teeth with a mouth opened or opens a mouth, in addition to primary image data scanning a face where the human closes the mouth and is kept silent, to be used as merge reference data of jawbone and the teeth. That is, the secondary image data are data scanning the face where the human opens the mouth to expose the teeth, and unlike the primary image data, includes the scan information of the teeth, such that it can become a reference for the combination upon alignment, and the control unit 110 can diagnose the occlusion state of the teeth and the state of the temporomandibular joint accurately and quickly by matching the teeth included in the secondary image data with the teeth data.

The control unit 110 transmits three-dimensional alignment data aligned with the trajectory data of the movement extraction unit 140 to the simulation unit 150.

Meanwhile, the simulation unit 150 outputs it through the output unit 180 by simulating so that the aligned three-dimensional alignment data move according to the trajectory data. In this time, when simulating the three-dimensional data in which the teeth data and the image data are aligned, the simulation unit 150 simulates the movement of the temporomandibular joint.

The simulation unit 150 displays the movement trajectory of the teeth data and an interference surface on a screen, and the control unit 110 detects the rotation shaft of the temporomandibular joint through the simulation.

The control unit 110 transmits the three-dimensional alignment data based on the trajectory data, the rotation shaft of the temporomandibular joint, the scan data, or the facial bone data photographed by the CT to the model generation unit 160.

The model generation unit 160 generates a teeth model reflecting the shape and movement of the teeth by designing the teeth based on the received alignment data, the trajectory data, and the simulation result (rotation shaft of the temporomandibular joint, etc.).

The model correction unit 170 determines whether or not interference occurs by testing the teeth model generated by the model generation unit 160 according to the trajectory data. The model correction unit 170 delivers information on the location where the interference occurs or the intensity thereof to the model generation unit 160 and accordingly, the model generation unit 160 generates a final teeth model that avoids the interference by applying data of the interference thereto.

Figure 2:
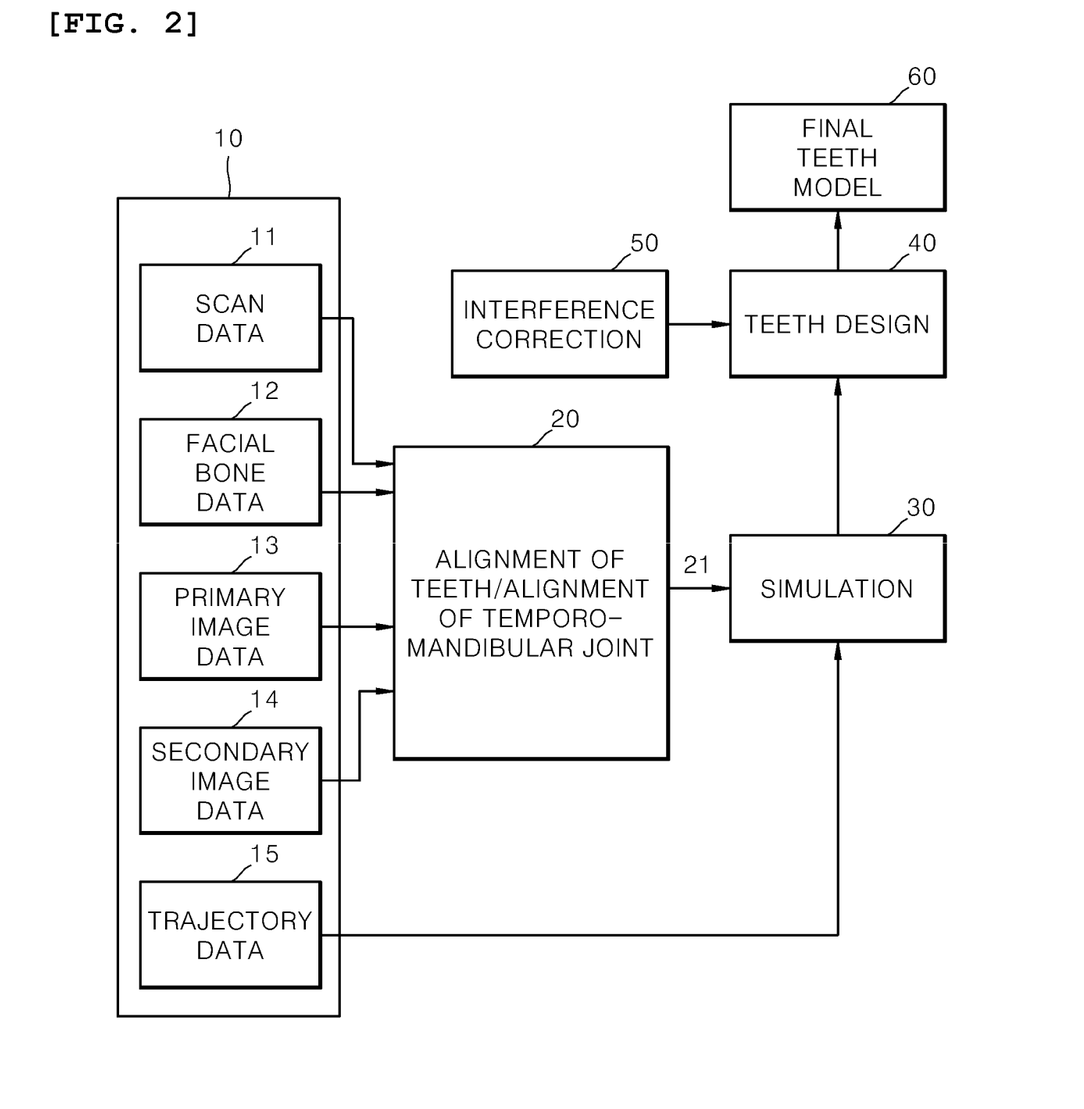
FIG. 2 is a diagram illustrating a data flow of the dental three-dimensional data processing device in accordance with the present disclosure.

FIG. 2 is a diagram illustrating a data flow of the dental three-dimensional data processing device in accordance with the present disclosure.

As illustrated in FIG. 2, the dental three-dimensional data processing device receives a plurality of data 10 through the input unit 120.

For example, scan data 11 through a dental scanner and facial bone data 12 having the shape of the teeth measured through a CT or a MRI are input as basic teeth data thereto. In this time, even if only any one of the scan data 11 of the teeth and the facial bone data 12 is input, the teeth state can be diagnosed.

In addition, primary and secondary image data 13, 14 of the human face are input through the input unit 120.

The primary and secondary image data are all data scanning the human face; and the primary image data are scan data photographed while the mouth is closed and the secondary image data are data that scan the face where the teeth are exposed, for example, that are photographed while the human bites the teeth with a mouth opened or opens the mouth.

The primary and secondary image data applies color texture to the three-dimensional data of the face, and is used to find a Frankfurt's plane, a Camper's plane, an occlusion reference plane (an occlusion plane), etc. In the secondary image data 14, a part of the teeth is included therein, such that it can become a reference for the combination upon alignment.

In addition, the trajectory data 15 of the teeth are input by tracking the movement of the teeth through the movement extraction unit 140.

Meanwhile, when aligning by using the scan data 11 of the teeth or the facial bone data 12, and the secondary image data 14 20, alignment data are generated 21.

Specifically, the alignment of the teeth is performed from the scan data 11 in the teeth data and the secondary image data 14, and the alignment of the temporomandibular joint is performed from the facial bone data 12 and the secondary image data 14.

The simulation unit 150 simulates the movement of the teeth of the three-dimensional data of the alignment data 21 based on the trajectory data 15 30.

Through the simulation, the movement of the teeth or the temporomandibular joint is displayed through the output unit 180, and the control unit 110 finds the shaft of the temporomandibular joint. Herein, for the alignment data of the teeth using the scan data 11 and the secondary image data 14, the control unit 110 finds the shaft of the temporomandibular joint based on the teeth data, and for the alignment data of the temporomandibular joint using the facial bone data 12 and the secondary image data 14, the control unit 110 finds the shaft of the temporomandibular joint from the CT data.

A teeth design 40 is performed based on the shaft of the temporomandibular joint detected through the simulation, the alignment data, and the trajectory data, and accordingly, a teeth model is generated. The model correction unit 170 inputs correction data 51 to the model generation unit 160 by detecting teeth interference, and accordingly, the model generation unit 160 generates a final teeth model for solving the teeth interference 60.

Figure 3:
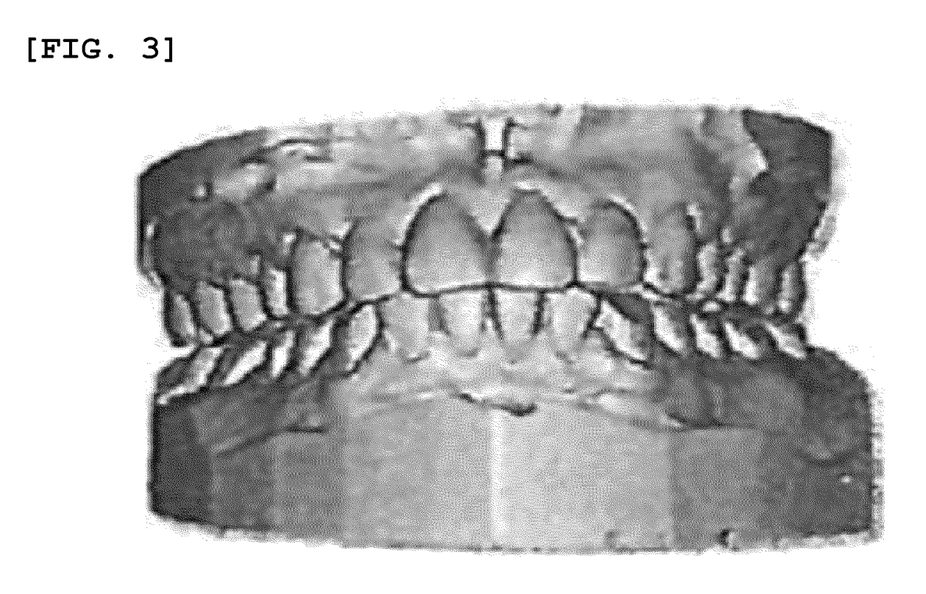
FIGS. 3 and 4 are diagrams illustrating an example of data processed by the dental three-dimensional data processing device in accordance with the present disclosure.
Figure 4:
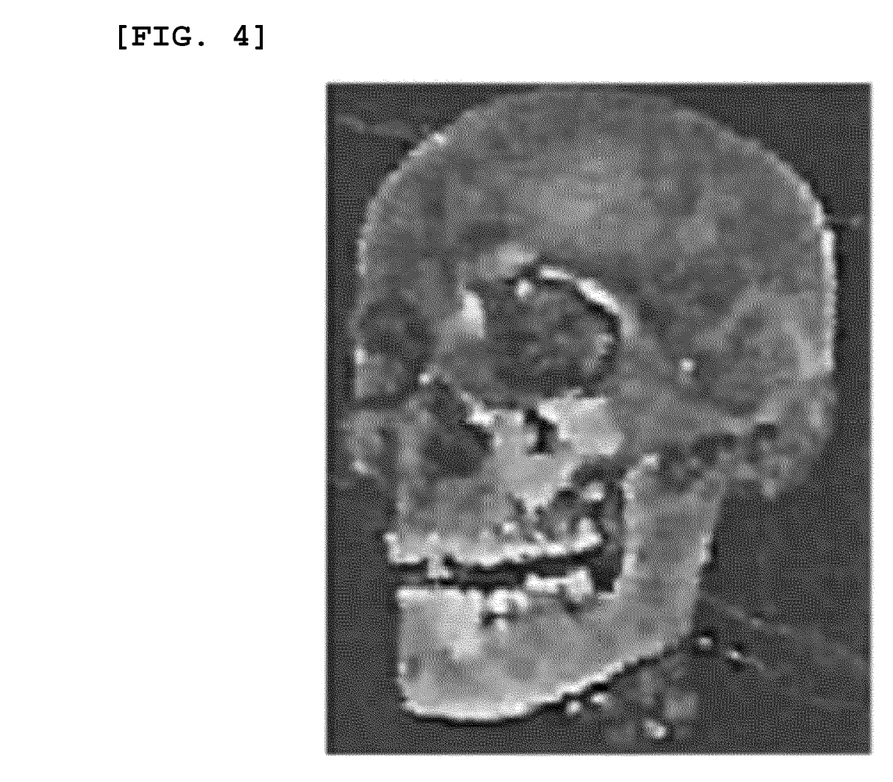

FIGS. 3 and 4 are diagrams illustrating an example of data processed by the dental three-dimensional data processing device in accordance with the present disclosure.

FIG. 3 illustrates three-dimensional scan data through a dental scanner in the teeth data, and the scan data are used for diagnosing the teeth. By generating the shape of the human teeth as a pattern to scan it through a three-dimensional scanner, it is input through the input unit 120.

In this time, the three-dimensional scan data of the teeth can be divided into data of maxillary and mandibular to be input thereto, respectively, and data where the maxillary and the mandibular are occluded can be generated through the secondary image data in the image data scanning the human face. When the data of the maxillary and the mandibular are separately input, the shape combined through alignment can be generated or the three-dimensional image data illustrated through a separate combination procedure can be generated.

FIG. 4 is acquired by CT photographing. Data of the teeth and the temporomandibular joint are included upon the CT photographing, such that the alignment of the temporomandibular joint and the simulation based on the temporomandibular joint are possible.

Figure 5:
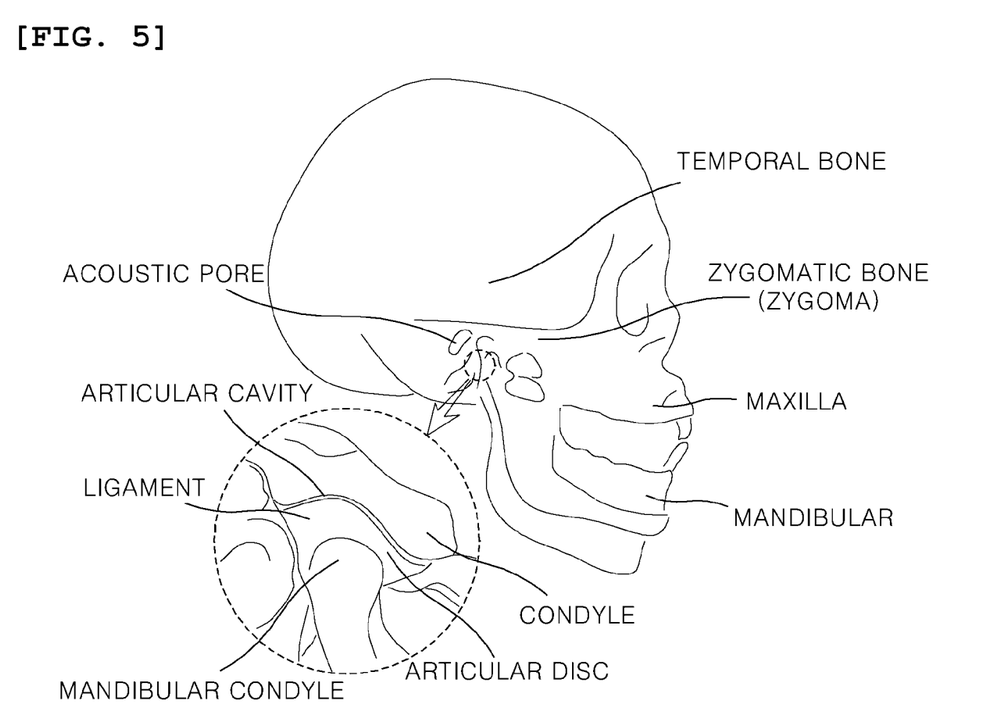
FIG. 5 is a diagram illustrating teeth and temporomandibular joint in a human skull.

FIG. 5 illustrates the teeth and the temporomandibular joint in a human skull, and the teeth, which are divided into maxilla and mandible, moves according to the movement of the temporomandibular joint to perform masticatory activity.

Accordingly, it is possible to generate the trajectory data for the movement thereof by tracking the movement of the teeth or the temporomandibular joint, thus solving interference when generating the teeth model or malocclusion.

As illustrated in FIG. 3, when the three-dimensional scan data of the teeth are used, the trajectory data for the movement of the teeth can be generated, and as illustrated in FIG. 4, when the facial bone data (the CT data) are used, the trajectory data for the movement of the temporomandibular joint can be generated.

Figure 6:
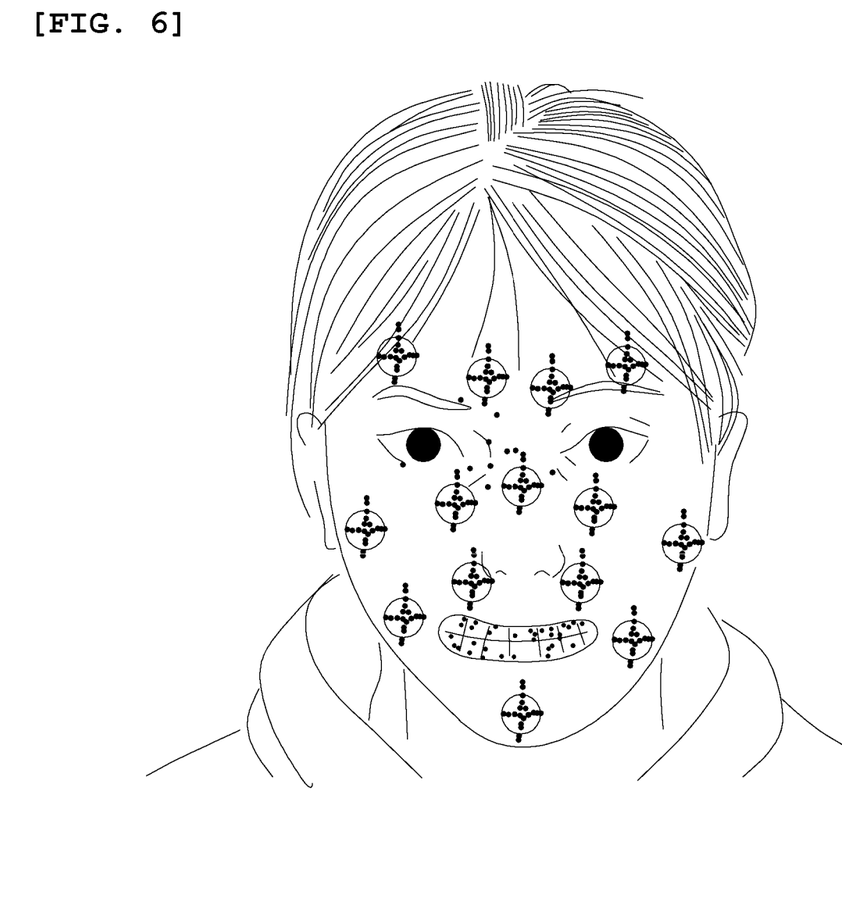
FIG. 6 is a diagram illustrating an example of a face scan of the dental three-dimensional data processing device in accordance with the present disclosure.

FIG. 6 is a diagram illustrating an example of a face scan of the dental three-dimensional data processing device in accordance with the present disclosure.

In order to acquire image data, when scanning a human face, as described above, an image where a human closes a mouth is scanned upon primary face scan, and as illustrated in FIG. 6, an image where the human bites the teeth with a mouth opened a little is scanned upon secondary scan.

In addition, as illustrated in FIG. 6, it is possible to track the movement of the teeth using the movement of a target by attaching the target to human teeth. Even if a target is not used separately, the movement of the teeth or the temporomandibular joint can be extracted through the movement of a feature point by extracting the feature point from the moving data.

When tracking the movement of the teeth or the temporomandibular joint using the image data, it is possible to extract the feature point in the image data and by tracking it, to track the movement of the entire teeth or temporomandibular joint. In addition, a method for extracting the movement of the teeth or the temporomandibular joint through the movement of the feature point is not only simple as compared with the method for attaching the target but also has relatively little interference with masticatory motion of the teeth.

When extracting the feature point from the image data, it is possible to extract the feature point using a Scale Invariant Feature Transform (SIFT) algorithm, etc. In addition, the feature point extracted from the image data can be used for aligning the location between the three-dimensional teeth data and the image data.

Figure 7:
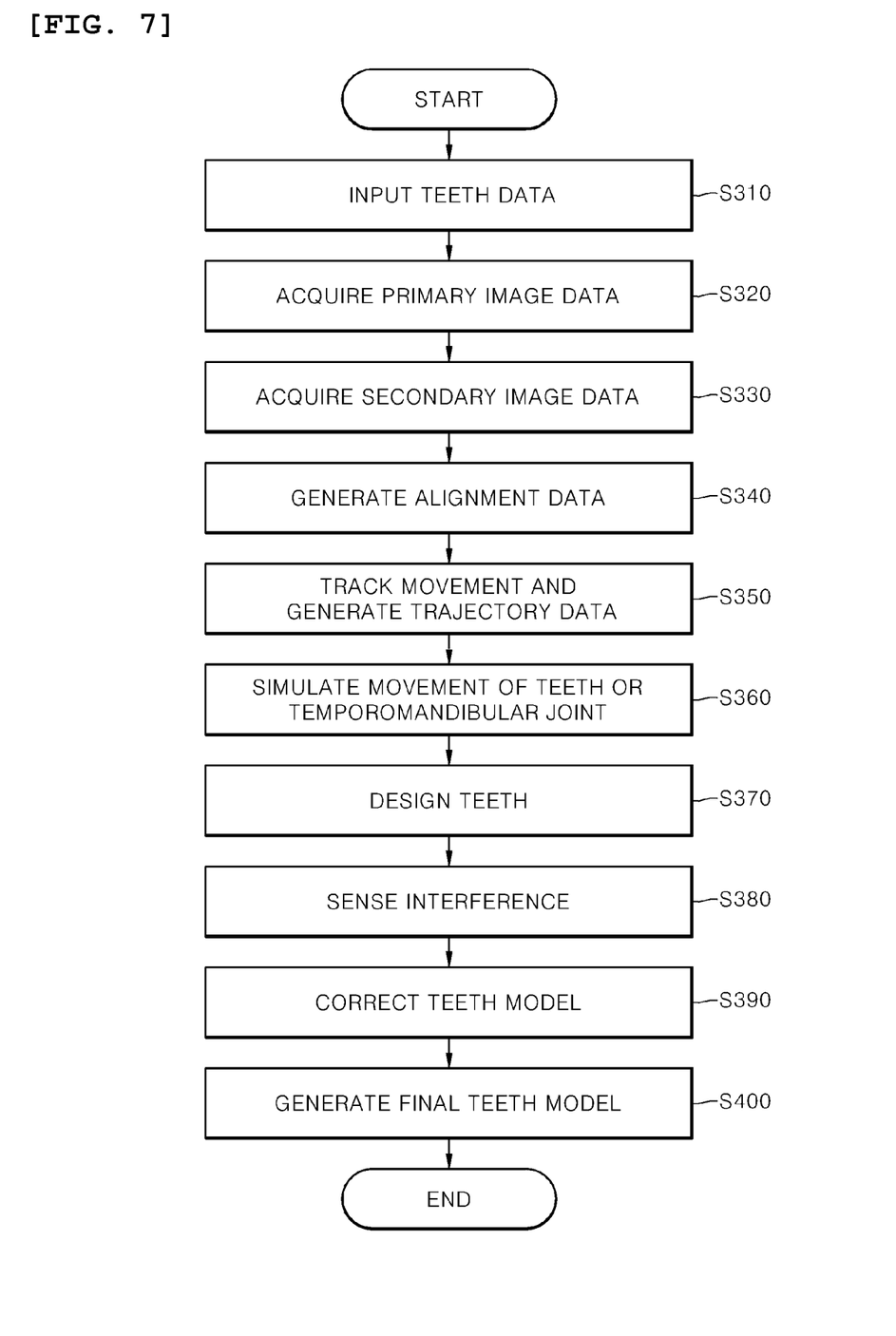
FIG. 7 is a flowchart illustrating a dental three-dimensional data processing method in accordance with the present disclosure.

FIG. 7 is a flowchart illustrating a dental three-dimensional data processing method in accordance with the present disclosure.

As illustrated in FIG. 7, the teeth data are input through the input unit 120 S310. In this time, the input unit 120 can be a scanner or a three-dimensional scanner, or can be connected to the scanner or the three-dimensional scanner to receive scanned data. In addition, the CT data separately photographed can be input thereto. That is, the teeth data use any one of the scan data through the dental scanner and the facial bone data having the shape of the teeth measured through a CT or a MRI.

In addition, primary image data are acquired by scanning a human face where a human closes a mouth and is kept silent S320, and secondary image data are acquired by scanning a human face where the human bites the teeth with the mouth opened or opens the mouth S330.

A distance is recognized through the primary image data, and facial three-dimensional data are generated by mapping color texture. In this time, the primary image data are used to find a Frankfurt's plane, a Camper's plane, or an occlusion reference plane.

In the secondary image data, the facial three-dimensional data having front teeth are generated as the front teeth or the mandible is scanned together. In some cases, upon secondary face scan, the teeth can be scanned by attaching a target thereto in order to detect it more easily.

Three-dimensional alignment data are generated by performing alignment using the teeth data and the image data of the face S340.

Specifically, the alignment of the teeth is performed by using the scan data through the dental scanner and the secondary image data. In addition, the CT data include the temporomandibular joint, such that the alignment of the temporomandibular joint is performed by using the facial bone data and the secondary image data. That is, the temporomandibular joint included in the facial bone data and one surface of the scanned teeth included in the secondary image data are aligned with each other. As described above, the three-dimensional data (hereinafter, the 'alignment data') of the teeth that are occlusion-aligned through the alignment are generated.

Thereafter, the movement extraction unit 140 generates the trajectory data by tracking the movement of the teeth or the temporomandibular joint S350.

The tracking of the movement of the teeth or the temporomandibular joint can be performed before scanning the teeth model, and can be also performed during the alignment. Specifically, the movement extraction unit 140 photographs or scans the moving human face in real time to receive it in real time, thus tracking the movement of the teeth or the temporomandibular joint. In this time, it is possible to track the movement of the teeth or the temporomandibular joint through the movement of a target by attaching the target to the teeth, or in addition, to track the movement by extracting the feature point without attaching the target thereto separately.

The movement extraction unit 140 generates the trajectory data by tracking the movement of the target or the feature point. Simulation is performed by applying the thus generated trajectory data to the alignment data or the occlusion-aligned three-dimensional data S360.

The simulation unit 150 displays it through the output unit 180 by reflecting the movement according to the trajectory data on the alignment data to simulate the masticatory activity of the human. The trajectory and an interference factor can be displayed together with the simulation data, and in addition, the rotation shaft of the temporomandibular joint can be detected through the simulation.

The model generation unit 160 designs the teeth considering the alignment data, the trajectory data, and the simulation result, that is, the interference factor and the rotation shaft of the temporomandibular joint S370.

The model correction unit 170 generates correction data by sensing the teeth interference of the teeth model generated through the teeth design once again using the trajectory S380.

The model generation unit 160 corrects the initially designed teeth model based on the correction data S390, and generates a final teeth model S400.

Accordingly, according to the present disclosure, the occlusion-aligned three-dimensional alignment data can be generated by combining and aligning the teeth data (the scan data through the dental scanner or the facial bone data) and the image data scanning the face, and the teeth model can be generated considering the trajectory of the movement or the interference by performing simulation using the movement of the teeth or the temporomandibular joint. In addition, it is possible to generate a final teeth model by solving the interference factor through the model correction, thus performing more precise diagnosis for the teeth state and generating the teeth model suitable for each human.

The present disclosure is not necessarily limited to these embodiments, as all the constituent elements constituting the embodiment of the present disclosure have been described as being combined and operating together. Within the scope of the present disclosure, depending on the embodiment, all of the components can operate selectively in combination with one or more.

The description above is merely illustrative of the technical idea of the present disclosure, and various modifications and changes can be made by those skilled in the art to which the present disclosure pertains without departing from the essential characteristics of the present disclosure.

According to the present disclosure, it is possible to manufacture the dental three-dimensional data processing device, which can extract the movements of the teeth and the temporomandibular joint to apply them to the teeth model, thus diagnosing the teeth state more accurately and precisely and analyzing the occlusion state according to the movements of the teeth and the temporomandibular joint, and can accurately analyze a patient's condition based on the movement and the occlusion state, thus establishing treatment measures.

The invention claimed is:

1. A dental three-dimensional data processing device, comprising:
   an input unit for receiving teeth data, and image data of a human face;
   a control unit for generating three-dimensional alignment data by combining and aligning the teeth data and the image data;
   a movement extraction unit for generating trajectory data by analyzing the movement of teeth or temporomandibular joint from the image data;
   a simulation unit for simulating the movement of the teeth or the temporomandibular joint by applying the trajectory data to the alignment data; and
   an output unit for outputting the results of simulating so that the alignment data moves according to the trajectory data in the simulation unit,
   wherein the simulation unit displays the movement trajectory of the teeth data and an interference surface on a screen, and
   wherein the control unit detects the rotation shaft of the temporomandibular joint through the simulation.

2. The dental three-dimensional data processing device of claim 1, wherein the teeth data comprises any one of scan data through a dental scanner, and facial bone data having the shape of the teeth measured through a Computed Tomography (CT) or a Magnetic Resonance Imaging (MRI).

3. The dental three-dimensional data processing device of claim 1, wherein the image data are successive data acquired in real time.

4. The dental three-dimensional data processing device of claim 1, further comprising a model generation unit for generating a teeth model reflecting the shape and movement of the teeth by designing the teeth based on the alignment data, the trajectory data, and the simulation result of the simulation unit.

5. The dental three-dimensional data processing device of claim 4, further comprising a model correction unit for delivering it to the model generation unit by determining an interference factor of the teeth model generated by the model generation unit.

6. The dental three-dimensional data processing device of claim 5, wherein the model correction unit inputs the correction data to the model generation unit by testing the teeth model according to the trajectory data to determine whether or not interference occurs.

7. The dental three-dimensional data processing device of claim 2, wherein the control unit aligns the scan data and the image data, and determines the occlusion state accordingly.

8. The dental three-dimensional data processing device of claim 2, wherein the control unit tracks the location and movement of the temporomandibular joint by aligning the facial bone data and the image data.

9. The dental three-dimensional data processing device claim 1, wherein the movement extraction unit extracts a feature point by analyzing the image data with respect to the moving teeth in real time, and detects the movement of the teeth by tracking the movement of the feature point.

10. The dental three-dimensional data processing device of claim 1, wherein the movement extraction unit detects the movement of the teeth by scanning a target attached to the teeth to analyze the movement of the target.

11. A dental three-dimensional data processing device, comprising:
   an input unit for receiving teeth data, and image data of a human face;
   a control unit for generating three-dimensional alignment data by combining and aligning the teeth data and the image data;
   a movement extraction unit for generating trajectory data by analyzing the movement of teeth or temporomandibular joint from the image data; and
   a simulation unit for simulating the movement of the teeth or the temporomandibular joint by applying the trajectory data to the alignment data,
   wherein the image data are image data scanning a face where the teeth are exposed, and
   wherein the control unit aligns them by matching the teeth included in the image data with the teeth data.

12. A dental three-dimensional data processing method, comprising:
   receiving teeth data including at least one of scan data through a dental scanner, and facial bone data having the shape of teeth measured through a CT or a MRI;
   receiving image data of a human face;
   generating alignment data by combining and aligning the teeth data including at least one of the scan data and the facial bone data, and the image data;
   generating trajectory data by analyzing the movement of the teeth or temporomandibular joint from the image data; and
   simulating the movement of the teeth or the temporomandibular joint by applying the trajectory data to the alignment data,
   wherein the image data comprises at least one of primary image data scanning a face where a human closes a mouth and is kept silent, and secondary image data scanning a face where human teeth are exposed,
   wherein the generating the alignment data aligns the teeth data and the image data by matching the human teeth included in the secondary image data with the teeth data.

13. The dental three-dimensional data processing method of claim 12, further comprising generating a teeth model reflecting the shape and movement of the teeth by designing the teeth in response to the alignment data, the trajectory data, and the simulation result.

14. The dental three-dimensional data processing method of claim 12, wherein the receiving the image data recognizes a distance using data scanning the human face, generates facial three-dimensional data as the image data by performing color texture mapping, and extracts a Frankfurt's plane, a Camper's plane, or an occlusion reference plane.

15. The dental three-dimensional data processing method of claim 12, wherein the generating the alignment data aligns the scan data and the image data, and determines the occlusion state accordingly.

16. The dental three-dimensional data processing method of claim 12, wherein the generating the trajectory data tracks the movement of the teeth or the temporomandibular joint from the image data input in real time.

17. The dental three-dimensional data processing method of claim 16, wherein the image data are data scanning a target attached to the teeth, and
   wherein the generating the trajectory data detects the movement of the teeth by detecting the target from the image data.

18. The dental three-dimensional data processing method of claim 16, wherein the generating the trajectory data extracts a feature point of the teeth from the image data, and generates the trajectory data by tracking the movement of the feature point.

19. The dental three-dimensional data processing method of claim 13, further comprising correcting the teeth model by sensing teeth interference using the trajectory data with respect to the teeth model.

* * * * *